US00PP27830P3

(12) United States Plant Patent
Shaw et al.

(10) Patent No.: US PP27,830 P3
(45) Date of Patent: Apr. 4, 2017

(54) STRAWBERRY PLANT NAMED 'CABRILLO'

(50) Latin Name: ***Fragaria×ananassa* Duch.**
Varietal Denomination: Cabrillo

(71) Applicant: The Regents of the University of California, Oakland, CA (US)

(72) Inventors: Douglas V. Shaw, Davis, CA (US); Kirk D. Larson, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 126 days.

(21) Appl. No.: 14/544,658

(22) Filed: Jan. 30, 2015

(65) Prior Publication Data

US 2016/0227687 P1 Aug. 4, 2016

(51) Int. Cl.
*A01H 5/08* (2006.01)

(52) U.S. Cl.
USPC ..... Plt./209

(58) Field of Classification Search
USPC ..... Plt./209
See application file for complete search history.

*Primary Examiner* — Keith Robinson
(74) *Attorney, Agent, or Firm* — Kilpatrick Townsend & Stockton LLP

(57) ABSTRACT

'Cabrillo' is a day-neutral strawberry cultivar that is moderate to strong in expressing the day-neutral character. 'Cabrillo' will be of special interest for winter plantings and in summer plantings where 'San Andreas', 'Portola', and 'Albion' have been successful.

3 Drawing Sheets

Genus and species: The strawberry cultivar of this invention is botanically identified as *Fragaria×ananassa* Duch.

Variety denomination: The variety denomination is 'Cabrillo'.

BACKGROUND OF THE INVENTION

This invention relates to a new and distinctive day-neutral type cultivar designated as 'Cabrillo', which resulted from a cross performed in 2008 between two unreleased germplasm accessions Cal 3.149-8 (unpatented) and Cal 5.206-5 (unpatented).

'Cabrillo' was first fruited at the University of California Wolfskill Experimental Orchard, near Winters, Calif. in 2009, where it was selected, originally designated Cal 8.181-1, and propagated asexually by runners. Following selection and during testing the plant of this selection was designated 'CN236'. With the decision that this plant was to be released, this plant was given the name 'Cabrillo' for purposes of introduction into commerce and for international registration and recognition. Asexual propagules from this original source have been tested at the Watsonville Strawberry Research Facility, the South Coast Research and Extension Center, and to a limited extent in grower fields starting in 2010.

BRIEF SUMMARY OF THE INVENTION

'Cabrillo' is a day-neutral (ever-bearing) strawberry cultivar similar to 'Albion' (U.S. Plant Pat. No. 16,228), but with higher yield. It is also similar to 'San Andreas' (U.S. Plant Pat. No. 19,975), but with higher yield, better flavor, and larger fruit. 'Cabrillo' is moderate to strong in expressing the day-neutral character and 'Cabrillo' will be of special interest for winter plantings and in summer plantings where 'San Andreas', 'Portola' (U.S. Plant Pat. No. 20,552), and 'Albion' have been successful. Fruiting plants of 'Cabrillo' are similar in morphology to 'Albion' or 'San Andreas', although slightly larger and more erect. The fruit shape for 'Cabrillo' is typically a short and either symmetrical or slightly flattened conic. It is easily distinguished by fruit shape from 'Albion' (long conic), 'San Andreas' (long conic with a slight neck) or 'Portola' (short and rounded conic). Subjectively, 'Cabrillo' has outstanding flavor. The fruit will be exceptional for both fresh market and processing, and will be useful for home garden purposes.

BRIEF DESCRIPTION OF THE DRAWINGS

The Figures depict various characteristics of the 'Cabrillo' cultivar. Plants were planted in November.

DETAILED DESCRIPTION OF THE INVENTION

Figure 1:
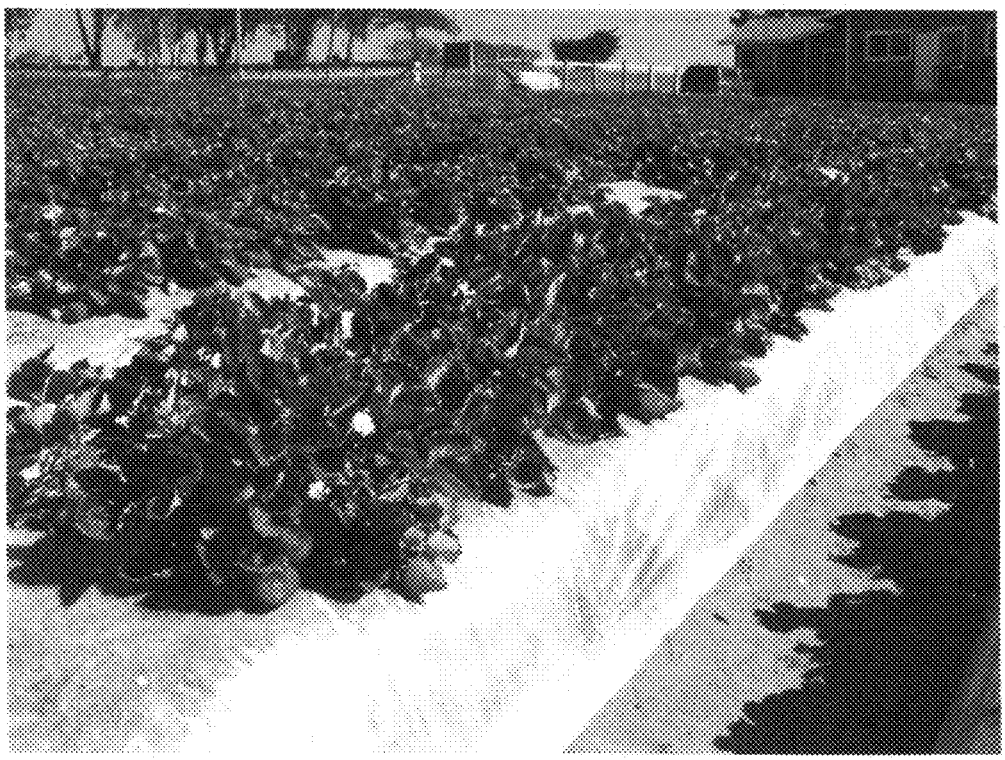
FIG. 1 shows the general flowering and fruiting characteristics of the plant in a field planting.
Figure 2:
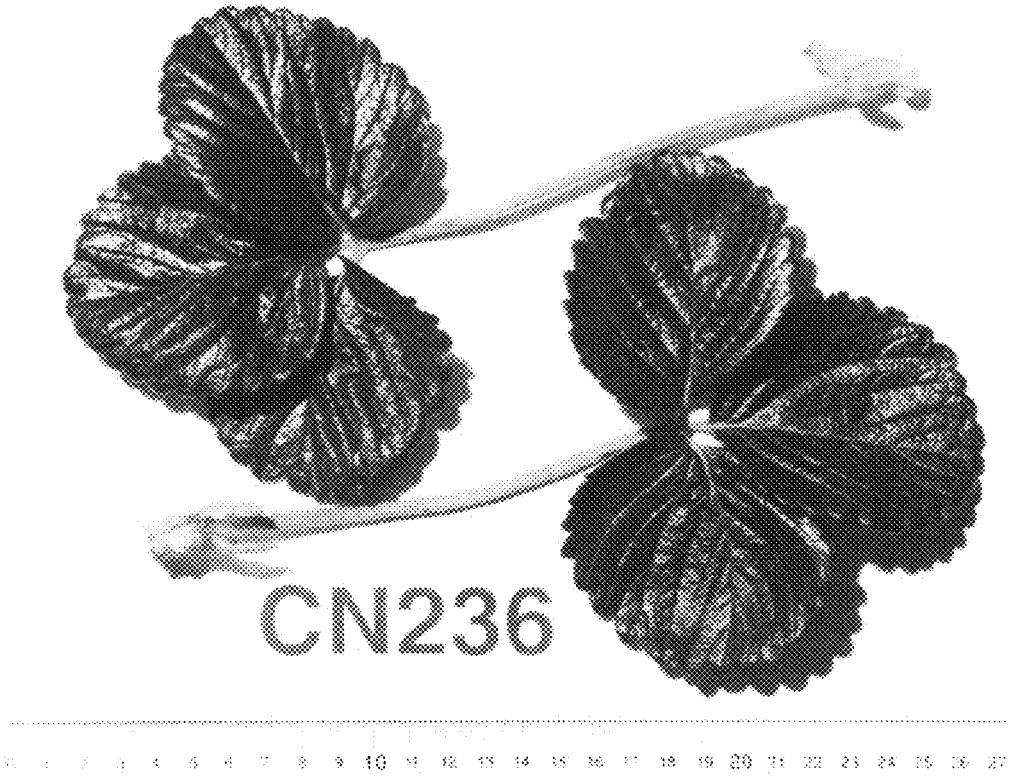
FIG. 2 shows a typical leaf at mid-season.
Figure 3:
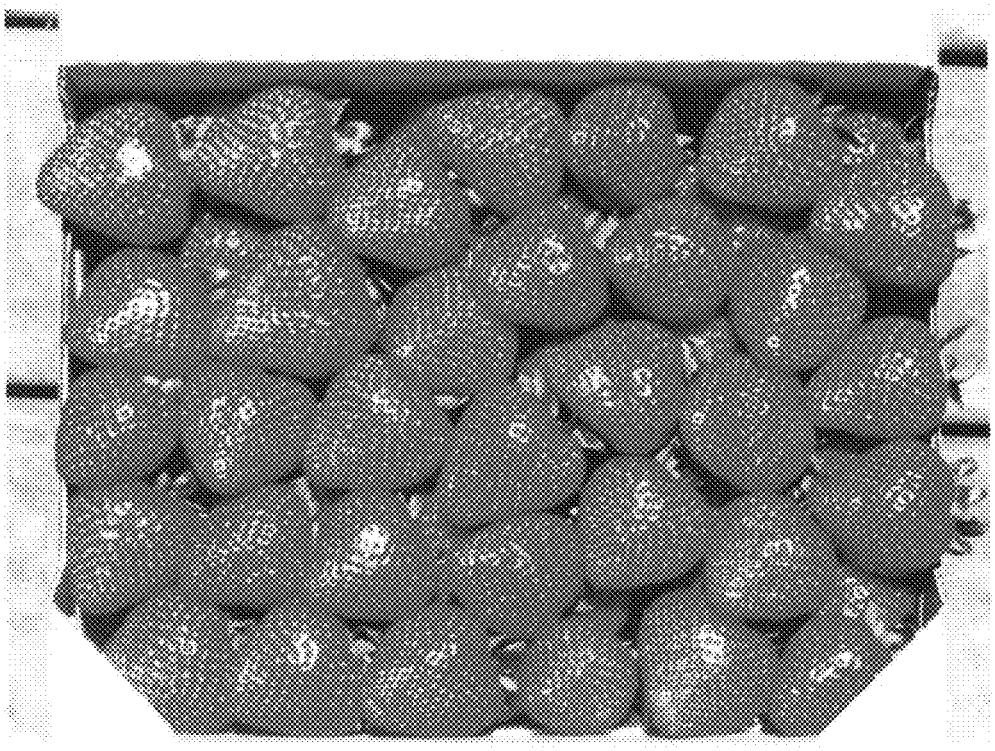
FIG. 3 shows representative mid-season fruit.

'Cabrillo' is typical of day-neutral strawberry cultivars and produces fruit regardless of day length when treated appropriately in arid, subtropical climates. 'Cabrillo' is moderate to strong in expressing the day-neutral character, being stronger in flowering response than 'San Andreas' and 'Albion', and less so than 'Portola' or 'Irvine' (U.S. Plant Pat. No. 7,172). The fruit of 'Cabrillo' is firmer and larger than that of unreleased parent Cal. 3.149-8; and larger and darker in color than the fruit of unreleased parent variety Cal. 5.206-5. 'Cabrillo' will be of special interest for winter plantings and in summer plantings where 'San Andreas', 'Portola', and 'Albion' have been successful.

Plants and Foliage:

Fruiting plants of 'Cabrillo' are similar in morphology to 'Albion' or 'San Andreas' although slightly larger and much more erect. The growth habit of the plant is upright. The inflorescence is at the same level in relation to foliage. Blistering of the leaf is absent or weak. Glossiness of the leaf is strong. The terminal leaflet is obtuse in shape. Comparative statistics for foliar characters near mid-season (November plantings) are given for 'Cabrillo' and the three comparison cultivars in Table 1. Individual leaflets for 'Cabrillo' are slightly smaller than for the comparison cultivars, and are much more concave. Leaves (including petioles) for 'Cabrillo' are slightly shorter than those for the comparison cultivars, mostly due to leaflet size. Petioles are generally thinner than those of the comparison cultivars. The adaxial (upper) and abaxial (lower) surfaces of leaves for 'Cabrillo' are similar in color to the comparison cultivars at mid-season.

TABLE 1

Foliar and plant characteristics for 'Cabrillo', 'Albion', 'San Andreas', and 'Portola'.

| | Cultivar | | | |
|---|---|---|---|---|
| Characteristic | 'Albion | 'San Andreas' | 'Portola' | 'Cabrillo' |
| Plant height (mm) | | | | |
| mean | 285 | 302 | 300 | 313 |
| range | 270-300 | 280-320 | 290-320 | 290-340 |
| Plant spread (mm) | | | | |
| mean | 390 | 444 | 433 | 452 |
| range | 335430 | 370-535 | 410-445 | 390-505 |
| Mid-tier leaflet Length (mm) | | | | |
| mean | 88 | 88 | 98 | 85 |
| range | 80-100 | 80-100 | 90-100 | 70-100 |
| Width | | | | |
| mean | 84 | 82 | 89 | 79 |
| range | 75-95 | 70-90 | 80-100 | 70-80 |
| Mid-tier leaf Length (mm) | | | | |
| mean | 132 | 135 | 134 | 126 |
| range | 110-150 | 130-150 | 150-180 | 120-140 |
| Width (mm) | | | | |
| mean | 164 | 154 | 170 | 160 |
| range | 150-180 | 130-160 | 150-180 | 140-180 |
| Leaf components Petiole length (mm) | | | | |
| mean | 205 | 220 | 223 | 218 |
| range | 180-220 | 200-260 | 190-260 | 200-240 |
| Petiole diameter (mm) | | | | |
| mean | 5.2 | 4.7 | 4.9 | 3.9 |
| range | 4-6 | 4-6 | 4-6 | 3-5 |
| Petiolule length (mm) | | | | |
| mean | 6.1 | 6.0 | 10.7 | 11.4 |
| range | | 5-9 | 10-12 | 8-14 |
| # leaflets/leaf | 3 | 3 | 3 | 3 |
| Leaf convexity | some flat, most slight concave | some flat, most slight concave | some flat, most slight concave | mostly concave |
| Serrations | | | | |
| number/leaf | 24.2 | 21.8 | 24.6 | 20.5 |
| range | 22-26 | 19-24 | 21-28 | 18-24 |

TABLE 1-continued

Foliar and plant characteristics for 'Cabrillo', 'Albion', 'San Andreas', and 'Portola'.

| | Cultivar | | | |
|---|---|---|---|---|
| Characteristic | 'Albion | 'San Andreas' | 'Portola' | 'Cabrillo' |
| shape | semi-pointed | semi-pointed | semi-pointed | semi-pointed |
| Leaf pubescence | moderate-heavy | moderate | moderate | light-moderate |
| Petiole pubescence density | heavy | heavy | moderate | heavy |
| direction | perpen-dicular | perpen-dicular | perpen-dicular | perpen-dicular |
| Petiole color (Munsell) | | 5 GY 8/8 | 7.5 GY 8/7 | 5 GY 8/8 |
| Stipule length (mm) | | | | |
| mean | 33.0 | 32.0 | 29.4 | 30.0 |
| range | 30-35 | 25-35 | 24-37 | 24-40 |
| Stipule color (Munsell) | | | | |
| core margins | 7 G 9/4<br>7 GY 8/7 | 2.5 GY 8/9<br>5 GY 8/7 | 2.5 GY 8/9<br>5 GY 8/8 | 5 GY 7/10<br>5 GY 8/8 |
| Stolon base diameter (mm) | 2.7 | 1.8 | 1.4 | 1.5 |
| Stolons per nursery mother plant | 15.8 | 21.5 | 20.3 | 22.0 |
| Venation | | | | |
| pattern | pinnate | pinnate | pinnate | pinnate |
| color (Munsell) | 5 GY 6/8 | 2.5 GY 6/8 | 2.5 GY 6/8 | 10 GY 8/7 |

Disease and Pest Reaction:

'Cabrillo' is moderately resistant to powdery mildew (*Sphaerotheca macularis*), and moderately susceptible to Anthracnose crown rot (*Colletotrichum acutatum*). It is moderately resistant to Verticillium wilt (*Verticillium dahliae*), Phytophthora crown rot (*Phytophthora cactorum*) and common leaf spot (*Ramularia tulasnei*) (Table 2). When treated properly, it has tolerance to two-spotted spider mites (*Tetranychus urticae*) equal to that for the comparison cultivars. 'Cabrillo' is tolerant to strawberry viruses encountered in California.

TABLE 2

Disease resistance scores for 'Cabrillo' and three comparison cultivars; scores were obtained in evaluations conducted in 2012-2014.

| Genotype | *Phytophthora* Resistance Score (5 = best) | *Verticillium* Resistance Score (5 = best) | *Colletotrichum* Resistance Score (5 = best) |
|---|---|---|---|
| 'Albion' | 4.6 | 4.0 | 2.9 |
| 'San Andreas' | 4.3 | 4.4 | 2.9 |
| 'Portola' | 4.4 | 3.2 | 7.4 |
| 'Cabrillo' | 4.2 | 3.4 | 1.8 |

Flowering, Fruiting, Fruit, and Production Characteristics:

'Cabrillo' is similar to other California day-neutral cultivars (e. g. 'San Andreas' and 'Albion') in that it will flower independently of day length, given appropriate temperature and horticultural conditions. The petals as arranged in the flower are touching. The achenes are level with the surface. The fruit is firm. Flowering occurs early. Comparative statistics for flower and fruit characters near mid-season (November plantings) are given for 'Cabrillo' and the three comparison cultivars in Table 4. The primary flowers for 'Cabrillo' are similar in size to the comparison cultivars with a calyx that is distinctly larger relative to the corolla on primary fruit. The calyx for 'Cabrillo' varies in position but is usually more indented than for 'Albion' or 'San Andreas', similar to 'Portola'. The fruit shape for 'Cabrillo' can vary, but is typically a short and either symmetrical or slightly flattened conic. It is easily distinguished by fruit shape from 'Albion' (long conic), 'San Andreas' (long conic with a slight neck) or 'Portola' (short and rounded conic). 'Cabrillo' usually has a greater proportion of symmetrical fruit than the comparison cultivars. External fruit color for 'Cabrillo' is lighter and has greater shine than that of 'Albion' or 'San Andreas' and is distinctly darker than that of 'Portola'. Internal color is somewhat lighter with less red pigment than for 'Albion' (Table 3). Achenes vary from yellow to dark red, but are frequently more yellow than the comparison cultivars, and are usually slightly indented.

TABLE 3

Foliar and fruit color characteristics for 'Cabrillo' and three comparison cultivars.

| | Cultivar | | | |
|---|---|---|---|---|
| Color Character | 'Albion' | 'San Andreas' | 'Portola' | 'Cabrillo' |
| Leaf color (CIELAB) Adaxial L* | | | | |
| mean | 36.3 | 36.9 | 37.7 | 36.2 |
| range | 32.2-40.8 | 34.1-39.2 | 36.2-38.7 | 35.0-38.7 |
| a* | | | | |
| mean | −9.8 | −9.7 | −9.4 | −9.8 |
| range | −6.7--12.8 | −8.5--10.9 | −6.9--10.8 | −6.7--12.5 |
| b* | | | | |
| mean | 13.7 | 13.1 | 13.2 | 12.9 |
| range | 12.1-18.1 | 12.8-15.5 | 10.8-14.3 | 10.1-15.8 |
| Munsell | 5 GY 4/3 | 5 GY 4/3 | 5 GY 3/2 | 5 GY 4/3 |
| Abaxial L* | | | | |
| mean | 50.2 | 49.4 | 48.7 | 51.1 |
| range | 48.7-60.0 | 37.8-51.3 | 45.8-50.0 | 49.2-53.1 |
| a* | | | | |
| mean | −13.1 | −12.6 | −12.2 | −13.1 |
| range | −11.5--14.0 | −9.9--13.8 | −11.2--12.7 | −12.5--14.0 |
| b* | | | | |
| mean | 20.1 | 20.6 | 18.7 | 20.4 |
| range | 16.8-22.9 | 13.2-21.6 | 18.1-19.1 | 19.5-21.0 |
| Munsell | 10 GY 7/8 | 10 GY 7/8 | 7.5 GY 5/7 | 5 GY 5/5 |
| Fruit color (CIELAB) External L* | | | | |
| mean | 37.6 | 40.3 | 40.1 | 39.2 |
| range | 34.6-41.5 | 37.7-44.9 | 37.2-42.5 | 35.4-41.6 |
| a* | | | | |
| mean | 34.2 | 35.7 | 35.1 | 32.0 |
| range | 29.9-38.4 | 33.2-37.8 | 33.9-36.9 | 30.8-32.8 |

TABLE 3-continued

Foliar and fruit color characteristics for 'Cabrillo' and three comparison cultivars.

| | Cultivar | | | |
|---|---|---|---|---|
| Color Character | 'Albion' | 'San Andreas' | 'Portola' | 'Cabrillo' |
| b* | | | | |
| mean | 19.3 | 23.2 | 22.5 | 70.5 |
| range | 12.9-20.9 | 18.6-30.0 | 15.2-27.2 | 18.5-23.2 |
| Munsell | 5 R 3/7 | 5 R 4/12 | 2.5 R 4/10 | 7.5 R 4/11 |
| Internal L* | | | | |
| mean | 49.4 | 56.2 | 52.8 | 54.4 |
| range | 37.2-54.4 | 54.2-59.1 | 48.6-57.6 | 50.0-56.0 |
| a* | | | | |
| mean | 19.2 | 18.5 | 18.4 | 14.9 |
| range | 16.7-23.1 | 12.8-20.8 | 13.5-21.8 | 9.8-20.5 |
| b* | | | | |
| mean | 23.1 | 25.2 | 27.6 | 22.1 |
| range | 20.0-27.9 | 22.0-28.1 | 23.4-30.3 | 18.2-29.4 |
| Munsell | 5 R 4/12 | 7.5 R 4/11 | 5 R 5/13 | 5 R 5/13 |
| Achene color Munsell | 2.5 R 8/12 | 10 Y 7/9 | 7.5 Y 7/9 | 10 Y 8/11 |

TABLE 4

Flower and fruit characters for 'Cabrillo' and three comparison cultivars.

| | Cultivar | | | |
|---|---|---|---|---|
| Character | 'Albion' | 'San Andreas | 'Portola' | 'Cabrillo' |
| Petal number | | | | |
| mean | 5.5 | 6.4 | 6.0 | 5.3 |
| range | 5-7 | 6-7 | 5-7 | 5-7 |
| Petal shape | | | | |
| apex | truncate to slightly obtuse | truncate to slightly obtuse | truncate to slightly obtuse | truncate to slightly obtuse |
| base | attenuate | attenuate | attenuate | attenuate |
| margin | entire | entire | entire | entire |
| Petal length (mm) | | | | |
| mean | 9.4 | 9.1 | 10.3 | 10/7 |
| range | 8-10 | 7-11 | 9-12 | 9-13 |
| Petal width (mm) | | | | |
| mean | 8.9 | 9.1 | 11.2 | 12.2 |
| range | 8-10 | 8-11 | 10-12 | 10-13 |
| Flower position (relative to foliage) | most even some exposed | most even some internal and exposed | most exposed, some even | most exposed |
| Calyx diam.(mm) | | | | |
| mean | 31.3 | 32.7 | 29.1 | 35.2 |
| range | 25-35 | 27-38 | 27-32 | 32-38 |
| Corolla diam. (mm) | | | | |
| mean | 26.0 | 30.8 | 24.2 | 26.3 |
| range | 25-30 | 28-34 | 22-26 | 24-28 |

TABLE 4-continued

Flower and fruit characters for 'Cabrillo' and three comparison cultivars.

| Character | Cultivar 'Albion' | 'San Andreas | 'Portola' | 'Cabrillo' |
|---|---|---|---|---|
| Sepal length (mm) | | | | |
| mean | 15.0 | 10.1 | 10.4 | 10.9 |
| range | 8-20 | 7-12 | 9-12 | 9-15 |
| Sepal width (mm) | | | | |
| mean | 6.5 | 6.4 | 6.9 | 6.7 |
| range | 5-8 | 5-10 | 6-8 | 5-8 |
| Sepal color (Munsell) | 5 GY 5/6 | 5 GY 5/6 | 5 GY 5/6 | 5 GY 5/6 |
| Pedicel length (mm) | | | | |
| mean | 261 | 301 | 266 | 243 |
| range | 240-280 | 260-350 | 220-300 | 230-270 |
| Pedicel diameter (mm) | | | | |
| mean | 4.5 | 4.9 | 3.9 | 5.0 |
| range | 4-5 | 4-7 | 3-5 | 4-6 |
| Pedicel color | 2.5 GY 6/8 | 2.5 GY 9/8 | 5 GY 6/8 | 2.5 GY 9/8 |
| Fruit shape | | | | |
| Fruit length (mm) | | | | |
| mean | 54.1 | 52.1 | 46.7 | 53.0 |
| range | 47-57 | 44-58 | 43-55 | 48-61 |
| Fruit width (mm) | | | | |
| mean | 45.7 | 44.2 | 47.4 | 47.7 |
| range | 42-48 | 42-55 | 42-52 | 43-57 |
| Length/width | | | | |
| ratio | 1.2 | 1.2 | 1.0 | 1.1 |
| range | 1.0-1.4 | 1.0-1.3 | 0.8-1.1 | 1.1-1.3 |
| subjective | medium to long conic | medium to long conic | most short conic | medium conic |
| Primary/secondary fruit comparison | | | | |
| size (subjective) | 70-80% | 60-70% | 60-70% | 70-80% |
| shape | shorter conic | shorter conic | similar shape | similar shape |
| Extent/size of hollow core | small-medium | small-medium | small-absent | small-absent |
| Calyx position | even to indented | even-slight neck | even-indented | indented-even |
| size relative to fruit | equal or greater than fruit diameter | equal or greater than fruit diameter | equal or greater than fruit diameter | equal or greater than fruit diameter |

TABLE 4-continued

Flower and fruit characters for 'Cabrillo' and three comparison cultivars.

| Character | Cultivar 'Albion' | 'San Andreas | 'Portola' | 'Cabrillo' |
|---|---|---|---|---|
| Seed position | even-indented | even | even | even-indented |
| Adherence of Calyx to Fruit | weak | weak | weak | intermediate |

Flower measurements and fruit measurements obtained May 1-Jun. 1, 2013, subjective observations obtained May 28, 2014.

'Cabrillo' has been tested under a variety of cultural regimes, and optimal performance is obtained when nursery treatments and nutritional programs similar to those for 'Albion', 'San Andreas', and 'Portola' are used. In general, 'Cabrillo' is more vigorous than the comparison cultivars and is more flexible to planting and chilling treatments. 'Cabrillo' retains excellent fruit quality in summer planting systems.

When treated with appropriate planting regimes, 'Cabrillo' has larger fruit and produces greater individual-plant yield than any of the comparison cultivars (Table 5). 'Cabrillo' has a similar production pattern to 'Albion' with most cultural treatments, although it is substantially more adapted to later-season winter planting and spring planting. Commercial appearance ratings have been similar to or better than those for all of the comparison cultivars, especially 'Portola'; these superior appearance scores translate directly into a larger fraction of marketable fruit than is produced by the comparison cultivars. Fruit for 'Cabrillo' is substantially firmer than fruit from the comparison cultivars. Subjectively, 'Cabrillo' has outstanding flavor. The fruit will be exceptional for both fresh market and processing, and will be useful for home garden purposes.

TABLE 5

Performance of 'Cabrillo' and three comparison cultivars evaluated at the Watsonville Research Facility in 2012-13. All plants for these trials were harvested from a commercial nursery near Macdoel, CA on October 15-16, and transplanted after 18-21 days supplemental storage. Fruit harvest was initiated in early April and continued through the first week of October. (52" 2-row beds, 17,300 plants/acre).

| Cultivar | Yield (g/plant) | Appearance Score (5 = best) | Fruit Size (g/fruit) | Firmness |
|---|---|---|---|---|
| 'Albion' | 2,632 | 4.1 | 32.6 | 12.2 |
| 'San Andreas' | 3,090 | 4.3 | 32.0 | 12.2 |
| 'Portola' | 2,900 | 3.4 | 31.7 | 11.4 |
| 'Cabrillo' | 3,669 | 4.3 | 32.0 | 12.2 |

What is claimed is:

1. A new and distinct cultivar of strawberry plant having the characteristics substantially as described and illustrated herein.

* * * * *